(12) United States Patent
Chen et al.

(10) Patent No.: US 9,850,213 B2
(45) Date of Patent: Dec. 26, 2017

(54) METHOD FOR PREPARING ROSUVASTATIN SODIUM

(71) Applicant: JiangXi Boya Seehot Pharmaceutical Co., Ltd., Fuzhou (CN)

(72) Inventors: Fener Chen, Shanghai (CN); Fangjun Xiong, Shanghai (CN); Jie Li, Shanghai (CN); Pingping Zhan, Shanghai (CN); Lingjun Xu, Shanghai (CN); Qiuqin He, Shanghai (CN); Wenxue Chen, Shanghai (CN); Xiayun Huang, Shanghai (CN); Yan Wu, Shanghai (CN)

(73) Assignee: JIANGXI BOYA SEEHOT PHARMACEUTICAL CO., LTD., Fuzhou (CN)

( * ) Notice: Subject to any disclaimer, the term of this patent is extended or adjusted under 35 U.S.C. 154(b) by 34 days.

(21) Appl. No.: 15/038,973

(22) PCT Filed: Jan. 10, 2014

(86) PCT No.: PCT/CN2014/070434
§ 371 (c)(1),
(2) Date: Dec. 19, 2016

(87) PCT Pub. No.: WO2015/074328
PCT Pub. Date: May 28, 2015

(65) Prior Publication Data
US 2017/0183314 A1    Jun. 29, 2017

(30) Foreign Application Priority Data

Nov. 25, 2013 (CN) .......................... 2013 1 0600552
Nov. 25, 2013 (CN) .......................... 2013 1 0601197

(51) Int. Cl.
*C07D 239/42* (2006.01)
(52) U.S. Cl.
CPC .................................. *C07D 239/42* (2013.01)
(58) Field of Classification Search
CPC .................................................. C07D 239/42
See application file for complete search history.

(56) References Cited

U.S. PATENT DOCUMENTS

| | | | |
|---|---|---|---|
| 2005/0080134 A1* | 4/2005 | Niddam-Hildesheim | C07D 239/42 514/548 |
| 2006/0004200 A1* | 1/2006 | Gudipati | C07D 319/06 544/310 |
| 2006/0089501 A1* | 4/2006 | Niddam-Hildesheim | C07D 239/42 544/332 |
| 2006/0149065 A1* | 7/2006 | Kumar | C07D 239/42 544/332 |
| 2007/0037979 A1* | 2/2007 | Niddam-Hildesheim | C07D 239/42 544/330 |
| 2007/0167625 A1* | 7/2007 | Balanov | C07D 239/42 544/332 |
| 2008/0091014 A1* | 4/2008 | Huang | C07D 239/42 544/297 |
| 2009/0069563 A1* | 3/2009 | Niddam-Hildesheim | C07C 69/675 544/297 |
| 2009/0124803 A1* | 5/2009 | Deshpande | C07D 239/42 544/322 |
| 2010/0228028 A1* | 9/2010 | Butters | C07D 239/30 544/297 |
| 2011/0295005 A1* | 12/2011 | Boerner | C07D 239/42 544/297 |

(Continued)

FOREIGN PATENT DOCUMENTS

SI    WO 2010081861 A1 *    7/2010 ........... C07D 239/42

OTHER PUBLICATIONS

Davidson et al., 3 Expert Opinion on Drug Safety, 547-557 (2004).*

*Primary Examiner* — Alexander R Pagano
(74) *Attorney, Agent, or Firm* — Kilpatrick Townsend & Stockton LLP

(57) ABSTRACT

The present invention belongs to the technical field of organic chemistry, and specifically relates to a method for preparing rosuvastatin sodium. The method of the invention comprises: reducing 4-p-fluorophenyl-6-isopropyl-2-(N-methyl-methylsulfonylamino)pyrimidine-5-carboxylic acid (VII) in the presence of a borohydride, an alkyl-substituted chlorosilane and an assistance in an organic solvent to prepare 4-p-fluorophenyl-5-hydroxymethyl-6-isopropyl-2-(N-methyl-methylsulfonylamino) pyrimidine (VIII); then performing a reaction of the compound VIII with a triphenyl phosphonium salt in an organic solvent to prepare a ((4-p-fluorophenyl-6-isopropyl-2-(N-methyl-methylsulfonylamino)-5-pyridyl)-methyl)triphenyl phosphonium salt (IX); performing a stereoselective Michael addition reaction of (S)-trans-4,5-dihydroxy-pent-2-olefine acid ester (II) with furfural (III) to prepare a 2-((4R,6S)-2-(furan-2-yl)-6-hydroxymethyl-1,3-dioxane-4-yl)acetate (IV); oxidizing the compound IV to prepare a 2-((4R,6S)-2-(furan-2-yl)-6-formacyl-1,3-dioxane-4-yl)acetate (V); performing an olefination reaction of the compound V with the (4-p-fluorophenyl-6-isopropyl-2-(N-methyl-methylsulfonylamino)pyrimid-5-yl)-methyl triphenyl substituted phosphonium salt (IX) or phosphate to prepare 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (VI); and performing deprotection and sodium salt formation of compound VI to prepare rosuvastatin sodium (I). The method has easily obtainable raw materials, and is simple to operate and suitable for industrial productions.

15 Claims, No Drawings

(56) References Cited

U.S. PATENT DOCUMENTS

2013/0018065 A1* 1/2013 Andrensek ........... C07D 239/42
514/275
2013/0066074 A1* 3/2013 Koftis .................. C07D 239/42
544/297

* cited by examiner

METHOD FOR PREPARING ROSUVASTATIN SODIUM

FIELD OF THE INVENTION

The present invention belongs to the technical field of organic chemistry, and specifically relates to a method for preparing rosuvastatin sodium.

BACKGROUND ARTS

Rosuvastatin calcium is a potent lipid-lowering drug for treating hypercholesteremia, and is known as "super-statin" internationally due to its minor side effect and being capable of reversing hardened artery blood vessels; in addition, rosuvastatin sodium is a precursor for synthesis of rosuvastatin calcium. The structural formula of rosuvastatin sodium is as represented by formula (I):

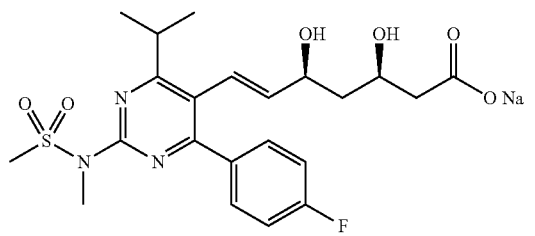

European patent EP 0521471 discloses a method for preparing rosuvastatin sodium (I) from a fully substituted pyrimidine aldehyde and a chiral C6 side chain Wittig reagent by Wittig olefination, deprotection, diastereoselective reduction, hydrolysis and salt formation.

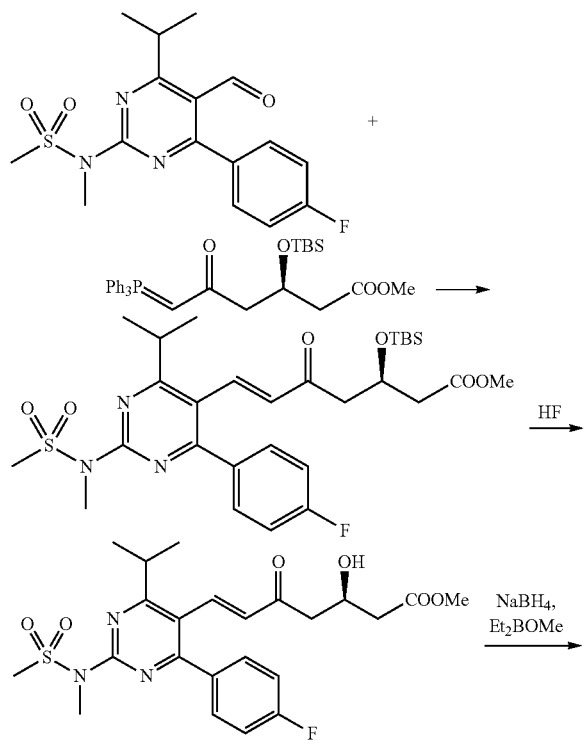

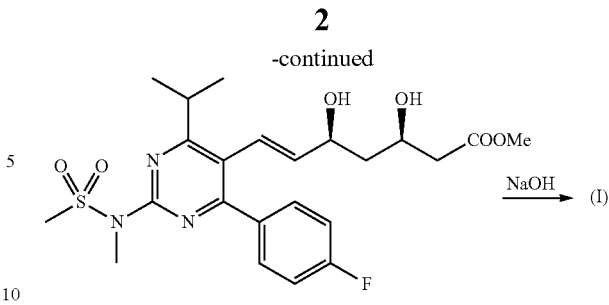

In this method, for the side chain, an expensive 3-tert-butyldimethysilyloxyglutaric anhydride is used as a raw material to establish a (3R)-stereocenter with a stoichiometric chiral auxiliary (−)-benzyl amygdalate, and an inflammable and explosive diethylmethoxyborane is used in the carbonyl reduction step, which brings about inconvenience to the industrial production, and also gives a high cost.

Patent WO 0049014 describes a method for preparing rosuvastatin sodium (I) from a fully substituted Wittig-Horner and a chiral C6 side chain aldehydeester by a Wittig-Horner reaction, deprotection, hydrolysis and salt formation.

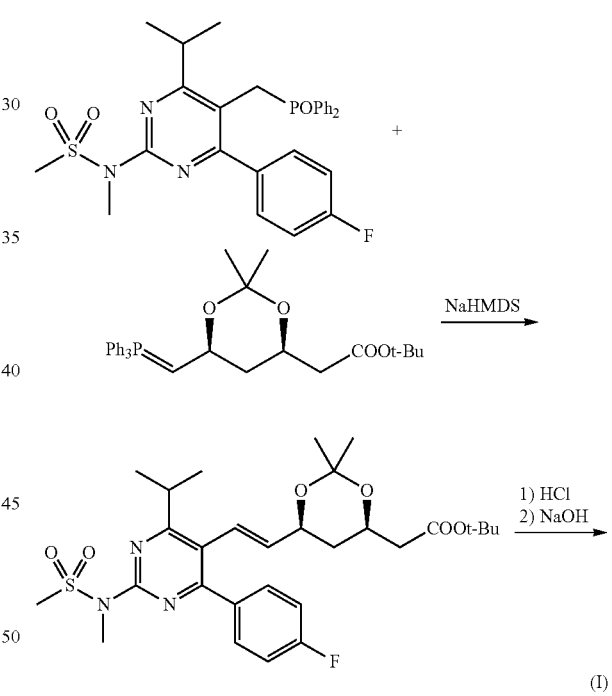

In the method, a large amount of highly toxic sodium cyanide and inflammable and explosive diethylmethoxyborane are used in the process of preparing the chiral C6 side chain aldehydeester. Moreover, in the Wittig-Horner procedure, the reaction must be performed at −75° C., under rigorous reaction conditions, which is disadvantageous for mass productions.

Patent WO 2004052867 discloses a method for preparing rosuvastatin sodium (I) from a fully substituted pyrimidine aldehyde and a chiral C6 cyano side chain Wittig reagent by Wittig olefination, deprotection, diastereoselective reduction, hydrolysis and salt formation.

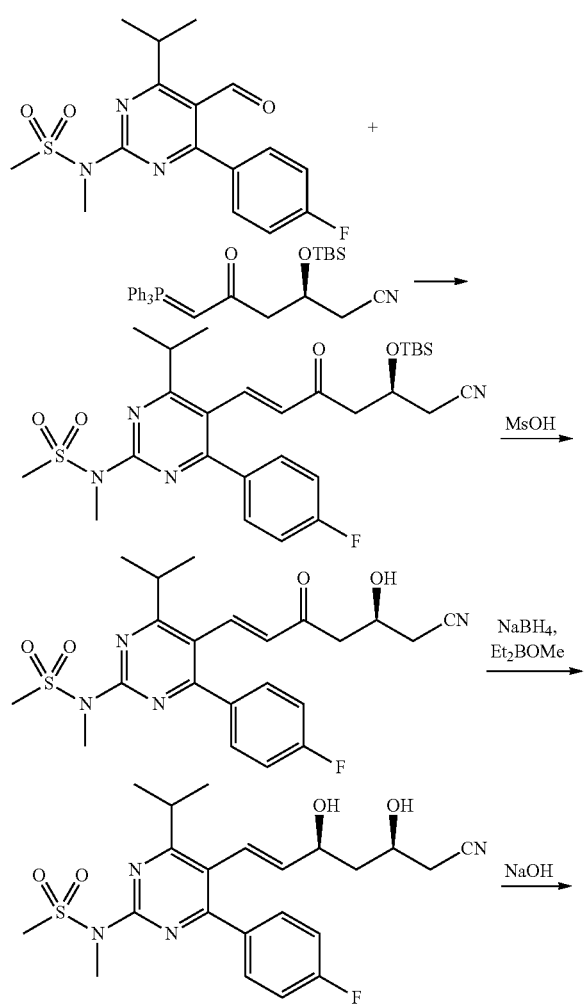

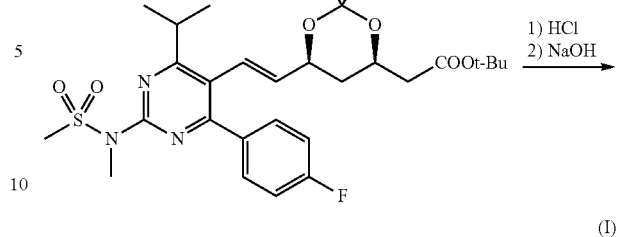

An expensive heavy metal palladium catalyst is used in this method, with high cost, and easy residues of the heavy metal.

World patent WO 2006076845 discloses a method for preparing rosuvastatin sodium (I) from a fully substituted pyrimidine aldehyde and diethyl cyanomethylphosphonate by Horner-Wadsworth-Emmons olefination, then reduction, catalyzed asymmetric Mukaiyama-Aldol condensation, diastereoselective carbonyl reduction, hydrolysis and salt formation.

The method has a long chiral C6 cyano side chain route, rigorous reaction conditions and a high raw material cost, lacking a practical meaning.

Patent WO 2006067456 describes a method for preparing rosuvastatin sodium (I) from a fully substituted pyrimidine bromide and a chiral C7 alkenyl ester by a palladium-catalyzed coupling reaction, deprotection, hydrolysis and salt formation.

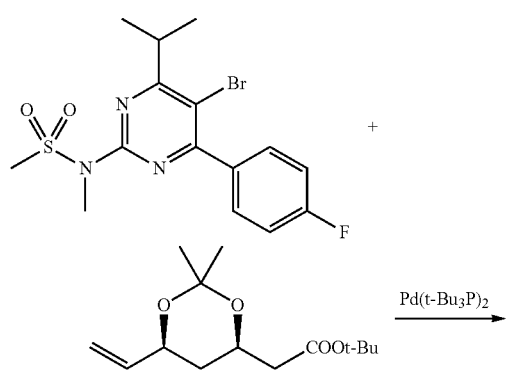

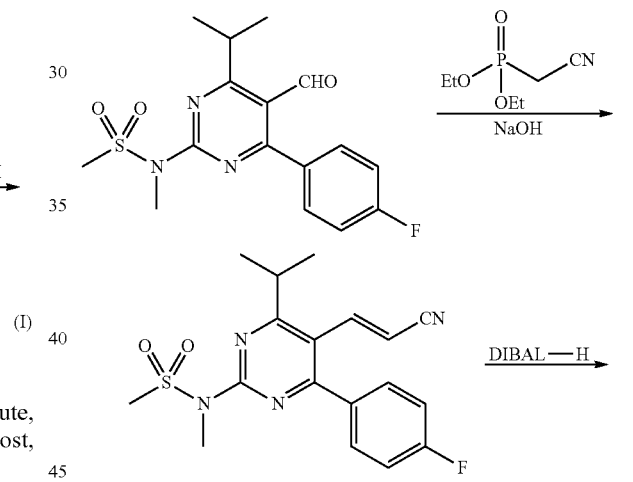

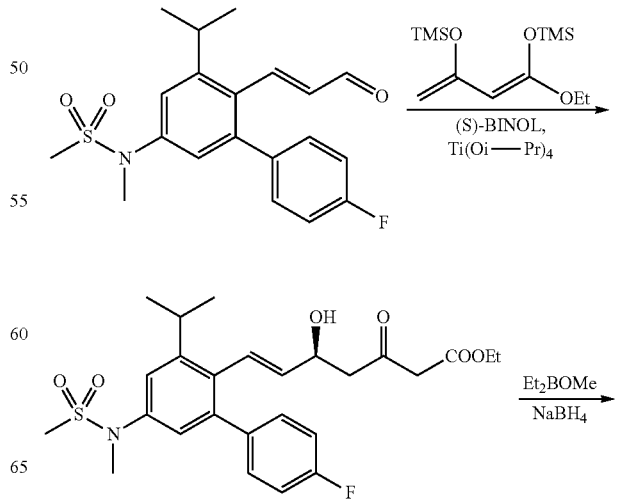

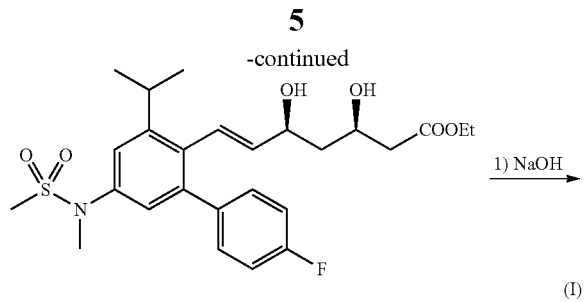

In this method, diisobutylaluminium hydride which is unavailable in China and expensive and inflammable and explosive diethylmethoxyborane are used in the two-step reduction procedure, respectively. Moreover, the reaction conditions for the preparation of a bis-enol disilyl ether are rigorous, which is not suitable for industrial production.

Chinese patent CN 102219780 discloses the preparation of rosuvastatin sodium (I) from a fully substituted pyrimidine aldehyde and a chiral C6 tetrazole sulfone ester by Julia-Kocienski olefination, aromatic nucleus nucleophilic substitution amination, deprotection and salt formation.

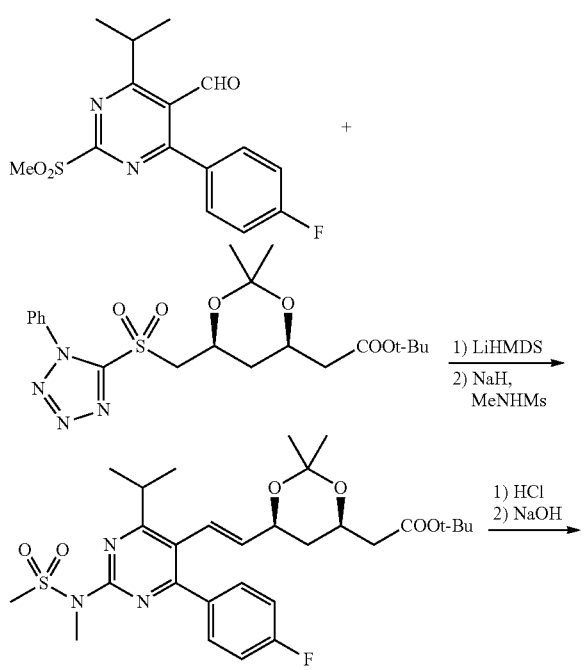

This method has a long reaction route for the chiral C6 tetrazole sulfone ester side chain, a high cost, and a poor atom economy; moreover, the Julia-Kocienski reaction must be performed at −60° C., the reaction condition being rigorous.

SUMMARY OF THE INVENTION

In order to overcome the defects in the prior art, the present invention provides an efficient method for preparing rosuvastatin sodium (I), which is suitable for industrial production.

The method for preparing rosuvastatin sodium (I) provided by the present invention has the specific steps as follows:

(1) reducing a compound of 4-p-fluorophenyl-6-isopropyl-2-(N-methyl-methylsulfonylamino)pyrimidine-5-carboxylic acid (VII) (with reference to patent WO 2012016479 for the synthesis of compound VII) by a borohydride in the presence of an alkyl-substituted chlorosilane and an assistant in an organic solvent at a reaction temperature of 0-100° C. for a reaction time of 6-72 h to prepare a compound of 4-p-fluorophenyl-5-hydroxymethyl-6-isopropyl-2-(N-methyl-methylsulfonylamino) pyrimidine (VIII);

(2) performing salt formation by a phosphorus substitution reaction of the compound VIII at a reaction temperature of 0-150° C. for a reaction time of 1-24 h to obtain a ((4-p-fluorophenyl-6-isopropyl-2-(N-methyl-methylsulfonylamino)-5-pyridyl)-methyl)triphenyl phosphonium salt (IX)

(3) performing a stereoselective Michael addition reaction of (S)-trans-4,5-dihydroxy-pent-2-enoate (II) with furfural (III) in the presence of a base to prepare 2-((4R,6S)-2-(furan-2-yl)-6-hydroxymethyl-1,3-dioxane-4-yl)acetate (IV) (with reference to document J. Org. Chem 2007, 72 (12): 4390-4395 for the synthesis of compound II);

(4) performing sodium hypochlorite oxidization of the compound (IV) in an organic solvent in the presence of sodium bicarbonate and potassium/sodium bromide under the catalysis of a 2,2,6,6-tetramethylpiperidine oxynitride to prepare 2-((4R,6S)-2-(furan-2-yl)-6-formacyl-1,3-dioxane-4-yl)acetate (V);

(5) performing an olefination reaction of the compound (V) with (4-p-fluorophenyl-6-isopropyl-2-(N-methyl-methylsulfonylamino)pyrimid-5-yl)-methyl substituted phosphonium salt (IX) or phosphate (the (4-p-fluorophenyl-6-isopropyl-2-(N-methyl-methylsulfonylamino)pyrimid-5-yl)-methyl substituted phosphate can be prepared with reference to patent WO 2010047296) in the presence of a base to prepare 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (VI) (with reference to documents for the synthesis of the (4-p-fluorophenyl-6-isopropyl-2-(N-methyl-methylsulfonylamino)pyrimid-5-yl)-methyl substituted phosphate); and (6) performing acid hydrolysis deprotection of the compound (VI) and sodium salt formation with a base to prepare rosuvastatin sodium (I).

The synthetic route is as follows:

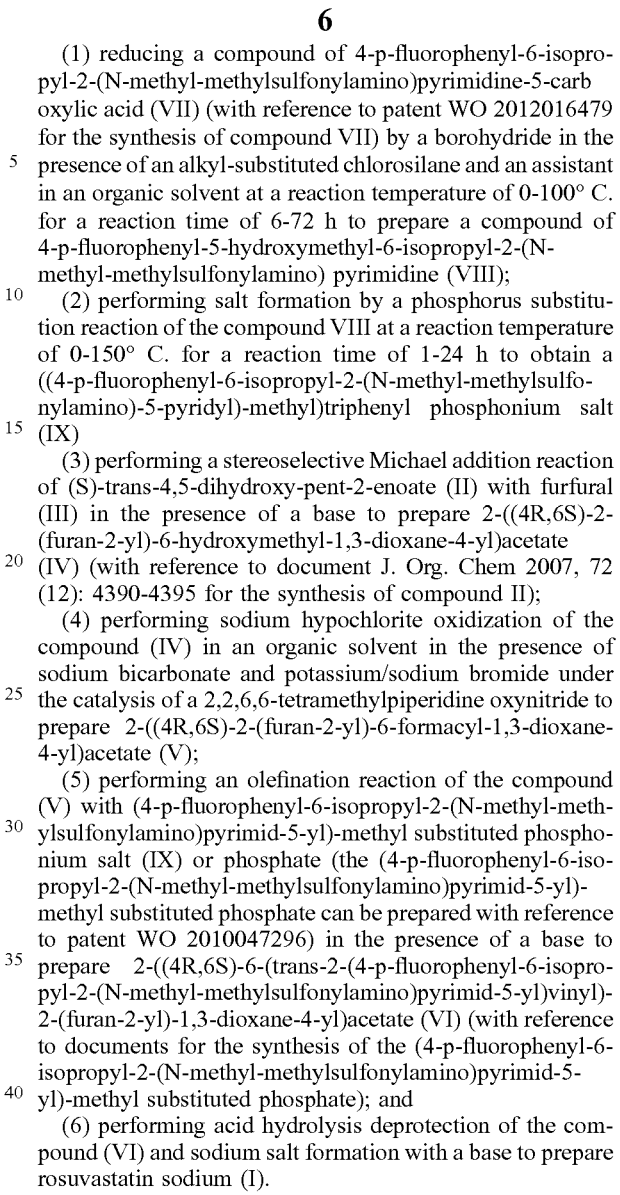

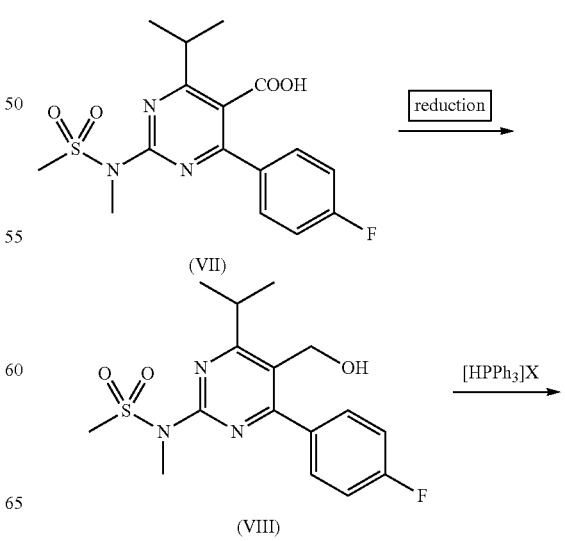

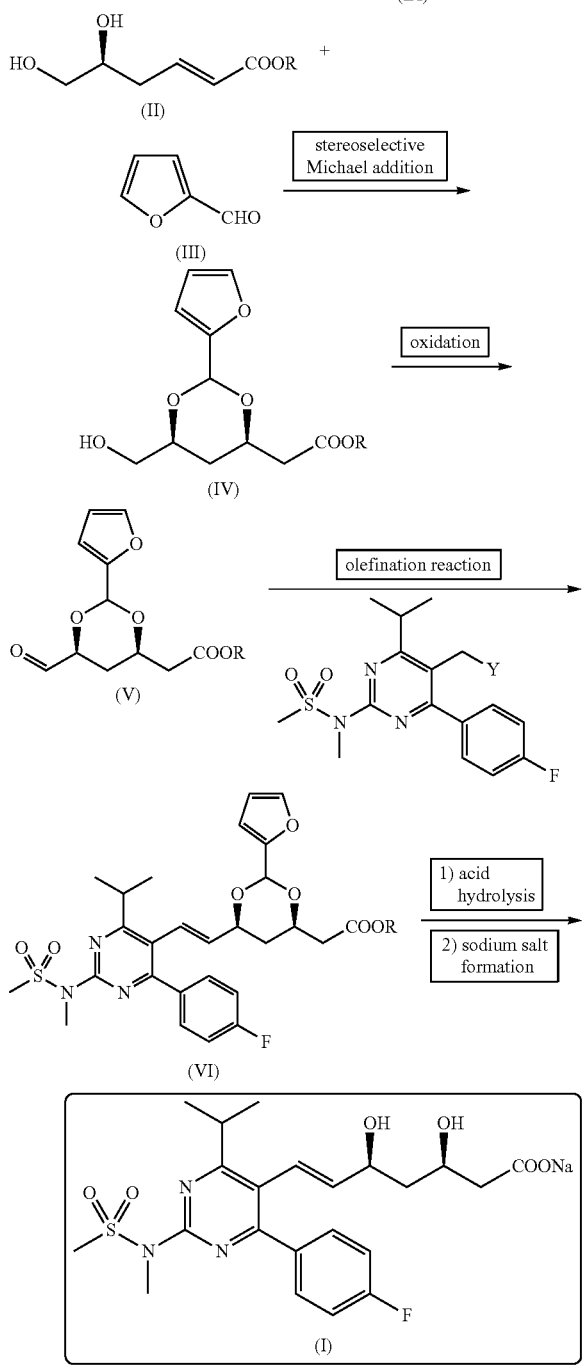

wherein Y is PPh₃X or —PO(OR')₂; X is bromine or boron tetrafluoride; R' is ethyl or isopropyl; and R is a $C_1$-$C_4$ linear or branched alkyl group.

In step (1) of the present invention, a compound of 4-p-fluorophenyl-6-isopropyl-2-(N-methyl-methylsulfonylamino)pyrimidine-5-carboxylic acid (VII) is reduced by a borohydride in the presence of an alkyl-substituted chlorosilane and an assistant in an organic solvent to prepare a compound of 4-p-fluorophenyl-5-hydroxymethyl-6-isopropyl-2-(N-methyl-methylsulfonylamino) pyrimidine (VIII). The borohydride reducing agent used is sodium borohydride, potassium borohydride, lithium borohydride, zinc borohydride or calcium borohydride, or aluminium borohydride, lithium borohydride, zinc borohydride or calcium borohydride formed in situ in the reaction system by sodium borohydride or potassium borohydride with aluminium chloride, lithium chloride, lithium bromide, zinc chloride or calcium chloride. The alkylchlorosilane used has a structural formula of:

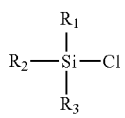

wherein $R_1$, $R_2$ and $R_3$, which are the same or different, are respectively a $C_1$-$C_4$ alkyl group. The assistant used is ceramic debris, glass cullet, gravel or water-washed stone, or processed ceramic beads, glass beads or steel beads. The solvent employed may be a single solvent of or a mixed solvent, in any ratio, of diethyl ether, methyl tert-butyl ether or isopropyl ether, or tetrahydrofuran, 1,4-dioxane, ethylene glycol methyl ether, ethylene glycol dimethyl ether or glycol dimethyl ether. The reaction temperature is 0-100° C., and the reaction time is 6-72 h.

In step (2) of the present invention, salt formation by phosphorus substitution reaction of the compound (VIII) with triphenyl phosphonium salt is performed in an organic solvent at a reaction temperature of 0-150° C. for a reaction time of 1-24 h to obtain a ((4-p-fluorophenyl-6-isopropyl-2-(N-methyl-methylsulfonylamino)-5-pyridyl)-methyl)triphenyl phosphonium salt (IX). The triphenyl phosphonium salt used is triphenyl phosphonium hydrobromide or triphenyl phosphonium fluoroborate. The solvent used may be a single solvent of or a mixed solvent, in any ratio, of a $C_1$-$C_4$ polyhalogenated alkane, acetonitrile, benzene, or a $C_1$-$C_3$ alkyl monosubstituted or polysubstituted benzene.

In step (3) of the present invention, when preparing a compound IV by a stereoselective Michael addition reaction of the compound II and compound III, the base used is any one of a $C_1$-$C_4$ alkoxide of an alkali metal, such as sodium methoxide, sodium ethoxide, potassium tert-butoxide, or a hexamethyl disilylamide of an alkali metal, such as potassium hexamethyl disilylamide, potassium hexamethyl disilylamide, etc. The molar ratio of the compound II to compound III to the base is 1:1-3:0.1-1.2. The organic solvent used may be a single solvent of or a mixed solvent, in any ratio, of a $C_1$-$C_4$ alkane symmetric or asymmetric ether (such as diethyl ether, isopropyl ether, and methyl tert-butyl ether), tetrahydrofuran or dioxane. The reaction temperature is −40-20° C.

In step (4) of the present invention, the compound IV undergoes sodium hypochlorite oxidization in an organic solvent in the presence of sodium bicarbonate and potassium/sodium bromide under the catalysis of a 2,2,6,6-tetramethylpiperidine oxynitride to prepare a compound V. The molar ratio of compound IV to the catalyst 2,2,6,6-tetramethylpiperidine oxynitride is 1:0.001-0.05. The organic solvent used may be a single solvent of or a mixed solvent, in any ratio, of a $C_5$-$C_{10}$ alkane or cycloalkane (such as petroleum ether, n-hexane, cyclohexane), a haloalkane (such as dichloromethane, 1,2-dichloroethane), or an arene (such as toluene, xylene). The reaction temperature is −15-10° C.

In step (5) of the present invention, when preparing a compound VI by olefination of the compound V and substituted phosphonium salt (IX), the base used is any one of an alkali metal hydroxide (such as sodium hydroxide, potassium hydroxide), an alkali metal carbonate (such as potassium carbonate), a $C_1$-$C_4$ alkoxide of an alkali metal (such as sodium methoxide, potassium tert-butoxide), and an alkali metal hydride (such as sodium hydride). The molar ratio of the compound V to the substituted phosphonium salt (IX) or phosphate to the base is 1:0.8-1.2:1-3. The organic solvent used in the reaction is a single solvent of or a mixed solvent, in any ratio, of tetrahydrofuran, dioxane, a halogenated alkane (such as dichloromethane, 1,2-dichloroethane), an arene (such as toluene, xylene), acetonitrile, dimethylsulfoxide, N,N-dimethylformamide or N-methylpyrrolidone. The reaction temperature is −80-100° C.

In step (6) of the present invention, when preparing a compound I from the compound VI by acid hydrolysis deprotection and then salt formation with a base, the acid used is any one of sulphuric acid, hydrochloric acid, trifluoroacetic acid, methylsulphonic acid and p-toluenesulphonic acid. The base used is any one of sodium hydroxide, sodium carbonate, and sodium methoxide and sodium ethoxide. The solvent used may be a single solvent of or a mixed solvent, in any ratio, of methanol, ethanol, acetonitrile, acetone, tetrahydrofuran, or water. the reaction temperature is 0-50° C.

The optimal conditions of the present invention are:

when preparing the compound VIII, the reducing agent is preferably sodium borohydride and potassium borohydride, the alkylchlorosilane is preferably trimethylchlorosilane, the assistant is preferably glass beads and steel beads, the solvent is preferably tetrahydrofuran and diethylene glycol dimethyl ether, the reaction temperature is preferably 20-80° C., and the reaction time is 12-36 h.

When preparing the compound IX, the solvent is preferably acetonitrile or toluene, the reaction temperature is preferably 20-110° C., and the reaction time is 4-18 h.

When preparing the compound IV, the base used is potassium tert-butoxide or sodium hexamethyl disilylamide. The molar ratio of the compound II to compound III to the base is 1:1-2:0.3-1.2. The organic solvent is tetrahydrofuran or diethyl ether. The reaction temperature is −40-0° C.

When preparing the compound V, the molar ratio of the compound IV to the 2,2,6,6-tetramethylpiperidine oxynitride is 1:0.001-0.01. The organic solvent used is dichloromethane. The reaction temperature is −10-5° C.

When preparing the compound VI, the base used is potassium carbonate, potassium tert-butoxide or sodium hydride. The molar ratio of the compound V to compound IX or phosphate to the base is 1:0.9-1.1:1-2. The organic solvent used is tetrahydrofuran, acetonitrile, toluene or dimethylsulfoxide. The reaction temperature is 50-80° C.

When preparing the compound I, the acid used is hydrochloric acid. The base used is sodium hydroxide. The solvent used is methanol, ethanol, or water. The reaction temperature is 20-40° C.

The method of the present invention has easily obtainable raw materials and moderate conditions, is simple and convenient to operate, and has an industrial value.

DETAILED DESCRIPTION OF THE INVENTION

The contents of the invention are further illustrated hereinafter by examples. However, the invention is not limited to the following examples.

Example 1

Synthesis of 4-p-fluorophenyl-5-hydroxymethyl-6-isopropyl-2-(N-methyl-methylsulfonylamino)pyrimidine (VIII)

Under the protection of nitrogen, sodium borohydride (0.38 g), dry tetrahydrofuran (40 mL) and glass beads (10 mL) are placed in a dry reaction flask, trimethylchlorosilane (2.1 g) is dropwise added under stirring at room temperature, after the completion of the addition, the temperature is increased to 60° C., stirring is performed for 3 h, then a suspension of 4-p-fluorophenyl-6-isopropyl-2-(N-methyl-methylsulfonylamino)pyrimidine-5-carboxylic acid VII (1.83 g) in tetrahydrofuran (5 mL) is added, and after the completion of the addition, the temperature is maintained under stirring for 24 h. After the completion of the addition, the reaction solution is cooled to 0-5° C., a saturated ammonium chloride solution is dropwise added slowly, and after the completion of the addition, the solution is stirred for 15 min, extracted using dichloromethane, washed with a 10% sodium carbonate solution, dried with anhydrous sodium sulphate, and subjected to solvent recovery under a reduced pressure to dryness to precipitate a solid, such that a white crystalline powder 4-p-fluorophenyl-5-hydroxymethyl-6-isopropyl-2-(N-methyl-methylsulfonylamino) pyrimidine is obtained (1.62 g, 92%), mp 137-139° C., $^1$H NMR (400 MHz, CDCl$_3$): δ 7.79-7.82 (m, 2H), 7.15 (t, J=8.4 Hz, 2H), 4.63 (s, 2H), 3.56 (s, 3H), 3.47-3.54 (m, 4H), 1.84 (br, 1H), 1.33 (d, J=6.8 Hz, 6H).

Example 2

Synthesis of 4-p-fluorophenyl-5-hydroxymethyl-6-isopropyl-2-(N-methyl-methylsulfonylamino)pyrimidine (VIII)

Under the protection of nitrogen, potassium borohydride (0.54 g), dry tetrahydrofuran (40 mL) and steel beads (10 mL) are placed in a dry reaction flask, trimethylchlorosilane (1.1 g) is dropwise added under stirring at room temperature, after the completion of the addition, heating is performed to 65° C., reflux stirring is performed for 3 h, then a suspension of 4-p-fluorophenyl-6-isopropyl-2-(N-methyl-methylsulfonylamino)pyrimidine-5-carboxylic acid VII (1.83 g) in tetrahydrofuran (5 mL) is added, and after the completion of the addition, the temperature is maintained under stirring for 30 h. After the completion of the addition, the reaction solution is cooled to 0-5° C., a saturated ammonium chloride solution is dropwise added slowly, and after the completion of the addition, the solution is stirred for 15 min, extracted using dichloromethane, washed with a 10% sodium carbonate solution, dried with anhydrous sodium sulphate, and subjected to solvent recovery under a reduced pressure to dryness to precipitate a solid, such that a white crystalline powder 4-p-fluorophenyl-5-hydroxymethyl-6-isopropyl-2-(N-methyl-methylsulfonylamino) pyrimidine is obtained (1.71 g, 97%).

Example 3

Synthesis of ((4-p-fluorophenyl-6-isopropyl-2-(N-methyl-methylsulfonylamino)-5-pyridyl)methyl) triphenyl phosphonium fluoroborate (IX) (X=BF$_4$)

A compound VIII (0.88 g) and triphenyl phosphonium fluoroborate (0.88 g) are dissolved in acetonitrile (20 mL), heated to 81° C., and subjected to reflux stirring for 24 h, and after the completion of the reaction, concentration under a reduced pressure is performed to dryness to obtain a white foamy solid IX (X=BF$_4$, 1.67 g, 97%), $^1$H NMR (400 MHz, CDCl$_3$): δ 7.74 (t, J=7.8 Hz, 3H), 7.54 (td, J=8, 3.2 Hz, 6H), 7.26 (t, J=6.8 Hz, 2H), 7.17 (dd, J=12.8, 7.8 Hz, 6H), 6.98 (t, J=8.4 Hz, 2H), 5.17 (d, J=12.4 Hz, 2H), 3.48 (s, 3H), 3.43 (s, 3H), 2.73 (sept., J=6.4 Hz, 1H), 0.88 (br, 6H).

Example 4

Synthesis of ((4-p-fluorophenyl-6-isopropyl-2-(N-methyl-methylsulfonylamino)-5-pyridyl)methyl) triphenyl phosphonium hydrobromate (IX) (X=Br)

A compound VIII (0.88 g) and triphenyl phosphonium hydrobromate (0.85 g) are placed in toluene (50 mL), heated to 81° C., and subjected to reflux stirring for 10 h, and after the completion of the reaction, cooling and leaving to stand are performed to precipitate a solid, and after filtration and drying, a white powdery solid IX is obtained (X=Br, 1.41 g, 83%), $^1$H NMR (400 MHz, DMSO-d6): δ 7.87 (m, 3H), 7.63 (m, 6H), 7.27 (m, 8H), 7.13 (t, J=8.4 Hz, 2H), 5.08 (d, J=13.6 Hz, 2H), 3.49 (s, 3H), 3.40 (s, 3H), 2.86 (m, 1H), 0.79 (d, J=4.4 Hz, 6H).

Example 5

Preparation of ethyl 2-((4R,6S)-2-(furan-2-yl)-6-hydroxymethyl-1,3-dioxane-4-yl)acetate (IV) (R=t-Bu)

(S)-tert-butyl trans-4,5-dihydroxylpent-2-enoate (2.02 g) and tetrahydrofuran (40 mL) are placed in a dry reaction flask and cooled to −20° C., furfural (2.00 g) is added, then potassium tert-butoxide (0.4 g*3) is added in three batches, after the completion of the addition, the temperature is maintained under stirring for 30 min, after the completion of the reaction, a saturated ammonium chloride solution (50 mL) is added, distillation is performed using water vapour, and the remainder is extracted using ethyl acetate, washed with a saturated table salt solution, dried by anhydrous sodium sulphate, and subjected to solvent recovery under a reduced pressure to obtain a light yellow oily solution IV (2.59 g, 87%, R=t-Bu), with a content of 94% (GC) and dr=97:3 (GC).

Example 6

Preparation of ethyl 2-((4R,6S)-2-(furan-2-yl)-6-hydroxymethyl-1,3-dioxane-4-yl)acetate (IV) (R=Et)

(S)-ethyl trans-4,5-dihydroxylpent-2-enoate (1.74 g) and tetrahydrofuran (40 mL) are placed in a dry reaction flask and cooled to −40° C., furfural (1.50 g) is added, then sodium hexamethyl disilylamide (1 mL*3, a 1 M tetrahydrofuran solution) is added in three batches, after the completion of the addition, the temperature is maintained under stirring for 30 min, after the completion of the reaction, a saturated ammonium chloride solution (50 mL) is added, distillation is performed using water vapour, and the remainder is extracted using ethyl acetate, washed with a saturated table salt solution, dried by anhydrous sodium sulphate, and subjected to solvent recovery under a reduced pressure to obtain a light yellow oily solution IV (2.21 g, 82%, R=Et), with a content of 95% (GC) and dr=95:5 (GC).

Example 7

Preparation of tert-butyl 2-((4R,6S)-2-(furan-2-yl)-6-hydroxymethyl-1,3-dioxane-4-yl)acetate (IV) (R=t-Bu)

(S)-tert-butyl trans-4,5-dihydroxylpent-2-enoate (2.02 g) and diethyl ether (40 mL) are placed in a dry reaction flask and cooled to −40° C., furfural (1.20 g) is added, then potassium tert-butoxide (0.4 g*3) is added in three batches, after the completion of the addition, the temperature is maintained under stirring for 30 min, after the completion of the reaction, a saturated ammonium chloride solution (50 mL) is added, distillation is performed using water vapour, and the remainder is extracted using ethyl acetate, washed with a saturated table salt solution, dried by anhydrous sodium sulphate, and subjected to solvent recovery under reduced pressure to obtain a light yellow oily solution IV (2.30 g, 77%, R=t-Bu), with a content of 96% (GC) and dr=98:2 (GC).

Example 8

Preparation of tert-butyl 2-((4R,6S)-2-(furan-2-yl)-6-formacyl-1,3-dioxane-4-yl)acetate (V) (R=t-Bu)

Tert-butyl 2-((4R,6S)-2-(furan-2-yl)-6-hydroxymethyl-1,3-dioxane-4-yl)acetate (1.49 g), 2,2,6,6-tetramethylpiperidine oxynitride (10 mg), potassium bromide (60 mg), sodium bicarbonate (4 g) and dichloromethane (30 mL) are placed in a reaction flask and cooled to −5° C., a sodium hypochlorite solution (10 mL, 6% of available chlorine) is dropwise added slowly, after the completion of the dropwise addition, the temperature is maintained under stirring for 2 h, after the completion of the addition, sodium hydrosulphite (2 g) is added and stirred for 30 min, extraction is performed using dichloromethane, and after washing with a saturated table salt solution, drying by anhydrous sodium sulphate and solvent recovery under reduced pressure, a yellow oily material V (1.38 g, 92%, R=t-Bu) is obtained, with a content of 93% (GC).

Example 9

Preparation of ethyl 2-((4R,6S)-2-(furan-2-yl)-6-formacyl-1,3-dioxane-4-yl)acetate (V) (R=Et)

Tert-butyl 2-((4R,6S)-2-(furan-2-yl)-6-hydroxymethyl-1,3-dioxane-4-yl)acetate (1.35 g), 2,2,6,6-tetramethylpiperidine oxynitride (2 mg), sodium bromide (50 mg), a saturated sodium bicarbonate solution (30 mL) and dichloromethane (30 mL) are placed in a reaction flask and cooled to 0° C., a sodium hypochlorite solution (10 mL, 6% of available chlorine) is dropwise added slowly, after the completion of the dropwise addition, the temperature is maintained under stirring for 3 h, after the completion of the addition, sodium hydrosulphite (2 g) is added and stirred for 30 min, extraction is performed using dichloromethane, and after washing with a saturated table salt solution, drying by anhydrous sodium sulphate and solvent recovery under a reduced pressure, a yellow oily material V (1.27 g, 94%, R=Et) is obtained, with a content of 90% (GC).

Example 10

Preparation of tert-butyl 2-((4R,6S)-2-(furan-2-yl)-6-formacyl-1,3-dioxane-4-yl)acetate (V) (R=t-Bu)

Tert-butyl 2-((4R,6S)-2-(furan-2-yl)-6-hydroxymethyl-1,3-dioxane-4-yl)acetate (1.49 g), 2,2,6,6-tetramethylpiperidine oxynitride (1 mg), potassium bromide (60 mg), sodium bicarbonate (4 g) and dichloromethane (30 mL) are placed in a reaction flask and cooled to −5° C., a sodium hypochlorite solution (10 mL, 6% of available chlorine) is dropwise added slowly, after the completion of the dropwise addition, the temperature is maintained under stirring for 3 h, after the completion of the addition, sodium hydrosulphite (2 g) is added and stirred for 30 min, extraction is performed using dichloromethane, and after washing with a saturated table salt solution, drying by anhydrous sodium sulphate and solvent recovery under a reduced pressure, a yellow oily material V (1.29 g, 87%, R=t-Bu) is obtained, with a content of 95% (GC).

Example 11

Preparation of tert-butyl 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (R=t-Bu, Y=PPh$_3$Br)

Tert-butyl 2-((4R,6S)-2-(furan-2-yl)-6-formacyl-1,3-dioxane-4-yl)acetate (1.60 g), (4-p-fluorophenyl-6-isopropyl-2-(N-methyl-methylsulfonylamino)pyrimid-5-yl)methyl)triphenyl phosphonium bromide (3.39 g), potassium tert-butoxide (1.7 g) and tetrahydrofuran (20 mL) are placed in a dry reaction flask, heated and undergo reflux stirring for 3 h under the protection of nitrogen, after the completion of the reaction, cooling is performed to room temperature, after solvent concentration under a reduced pressure, water is added (50 mL), extraction is performed using toluene, after washing with a saturated ammonium chloride solution, drying by anhydrous sodium sulphate, and solvent recovery under a reduced pressure to dryness, the remainder undergoes recrystallization using methanol to obtain a white solid VI (2.39 g, 78%, R=t-Bu), with a content of 98% (HPLC).

Example 12

Preparation of tert-butyl 2-((4R,6S)-6-(trans-2-(4-p-fluorophenyl-6-isopropyl-2-(N-methyl-methylsulfonylamino)pyrimidine-5-yl)vinyl)-2-(furan-2-yl)-1,3-dioxane-4-yl)acetate (R=t-Bu, Y=PPh$_3$Br)

Tert-butyl 2-((4R,6S)-2-(furan-2-yl)-6-formacyl-1,3-dioxane-4-yl)acetate (1.48 g), (4-p-fluorophenyl-6-isopropyl-2-(N-methyl-methylsulfonylamino)pyrimid-5-yl)methyl)triphenyl phosphonium bromide (3.39 g), anhydrous potassium carbonate (1.38 g) and acetonitrile (20 mL) are placed in a dry reaction flask, heated and undergo reflux stirring for 12 h under the protection of nitrogen, after the completion of the reaction, cooling is performed to room temperature, after solvent concentration under a reduced pressure, water is added (50 mL), extraction is performed using toluene, after washing with a saturated ammonium chloride solution, drying by anhydrous sodium sulphate, and solvent recovery under a reduced pressure to dryness, the remainder undergoes recrystallization using methanol to obtain a white solid VI (2.18 g, 70%, R=t-Bu), with a content of 99% (HPLC).

Example 13

Preparation of tert-butyl 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (R=Et, Y=PO(OEt)$_2$)

Ethyl 2-((4R,6S)-2-(furan-2-yl)-6-formacyl-1,3-dioxane-4-yl)acetate (1.47 g), diethyl (4-p-fluorophenyl-6-isopropyl-2-(N-methyl-methylsulfonylamino)pyrimid-5-yl)methyl)triphenyl phosphate (2.36 g), anhydrous potassium carbonate (1.38 g) and dimethylsulfoxide (20 mL) are placed in a dry reaction flask and stirred at 80° C. for 2 h under the protection of nitrogen, after the completion of the reaction, cooling is performed to room temperature, water is added (50 mL), extraction is performed using toluene, and after washing with a saturated ammonium chloride solution, drying by anhydrous sodium sulphate, and solvent recovery under a reduced pressure to dryness, the remainder undergoes recrystallization using methanol to obtain a white solid VI (2.38 g, 81%, R=Et), with a content of 99% (HPLC).

Example 14

Preparation of tert-butyl 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (R=t-Bu, Y=PO(OEt)$_2$)

Tert-butyl 2-((4R,6S)-2-(furan-2-yl)-6-formacyl-1,3-dioxane-4-yl)acetate (1.60 g), diethyl (4-p-fluorophenyl-6-isopropyl-2-(N-methyl-methylsulfonylamino)pyrimid-5-yl)methyl)triphenyl phosphate (2.36 g), sodium hydride (0.4 g, 60%) and toluene (20 mL) are placed in a dry reaction flask and stirred at 80° C. for 2 h under the protection of nitrogen, after the completion of the reaction, cooling is performed to 0° C., a saturated ammonium chloride solution is added slowly (20 mL), extraction is performed using toluene, and after washing with a saturated table salt solution, drying by anhydrous sodium sulphate, and solvent recovery under a reduced pressure to dryness, the remainder undergoes recrystallization using methanol to obtain a white solid VI (2.28 g, 74%, R=t-Bu), with a content of 99% (HPLC).

Example 15

Preparation of Rosuvastatin Sodium (I)

Tert-butyl 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (3 g) and methanol (30 mL) are placed in a reaction flask, 3 M hydrochloric acid (2 mL) is added and stirred at 35° C. for 3 h, after the completion of the reaction, the pH is adjusted by a saturated sodium bicarbonate solution to 7-8, after solvent recovery under a reduced pressure, water (20 mL) is added, extraction is performed using ethyl acetate, after drying by anhydrous sodium sulphate and solvent recovery under a reduced pressure to dryness, methanol (50 mL) and sodium hydroxide (0.19 g) are then added, stirred at room temperature for 2 h, and subjected to solvent recovery under a reduced pressure to dryness, diethyl ether (10 mL) is added to the remainder, after stirring, a solid is precipitated, and after filtration and drying, a white powdery solid I (2.30 g, 94%) is obtained. The content is 99% (HPLC), and the optical purity >99% ee.

Example 16

Preparation of Rosuvastatin Sodium (I)

Ethyl 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (3 g) and ethanol (30 mL) are placed in a reaction flask, 3 M hydrochloric acid (2 mL) is added and stirred at 35° C. for 3 h, after the completion of the reaction, the pH is adjusted by a saturated sodium bicarbonate solution to 7-8, after solvent recovery under a reduced pressure, water (20 mL) is added, extraction is performed using ethyl acetate, after drying by anhydrous sodium sulphate and solvent recovery under a reduced pressure to dryness, ethanol (50 mL) and sodium hydroxide (0.20 g) are then added, stirred at room temperature for 2 h, and subjected to solvent recovery under a reduced pressure to dryness, diethyl ether (10 mL) is added to the remainder, after stirring, a solid is precipitated, and after filtration and drying, a white powdery solid I (2.36 g, 92%) is obtained, with a content of 99% (HPLC) and an optical purity of >99% ee.

All the documents mentioned in the present invention are incorporated by reference in the present application, as if each document is alone incorporated by reference. In addition, it should be understood that after reading the above-mentioned teaching contents of the invention, a person skilled in the art would be able to make various modifications and amendments to the present invention, and these equivalent forms likewise falling within the scope defined by the appended claims of the present application.

The invention claimed is:

1. A method for preparing rosuvastatin sodium, comprising the steps of:
    (1) reducing a compound of 4-p-fluorophenyl-6-isopropyl-2-(N-methyl-methylsulfonylamino)pyrimidine-5-carboxylic acid (VII) in an organic solvent by a borohydride in the presence of an alkyl-substituted chlorosilane and an assistant at a reaction temperature of 0-100° C. for a reaction time of 6-72 h to prepare a compound of 4-p-fluorophenyl-5-hydroxymethyl-6-isopropyl-2-(N-methyl-methylsulfonylamino) pyrimidine (VIII);
    (2) performing salt formation by a phosphorus substitution reaction of compound VIII with a triphenyl phosphonium salt in an organic solvent at a reaction temperature of 0-150° C. for a reaction time of 1-24 h to obtain a ((4-p-fluorophenyl-6-isopropyl-2-(N-methyl-methylsulfonylamino)-5-pyridyl)-methyl)triphenyl phosphonium salt (IX);
    (3) performing a stereoselective Michael addition reaction of (S)-trans-4,5-dihydroxy-pent-2-enoate (II) with furfural (III) in the presence of a base to prepare 2-((4R,6S)-2-(furan-2-yl)-6-hydroxymethyl-1,3-dioxane-4-yl) acetate (IV);
    (4) performing a sodium hypochlorite oxidization of the compound IV in an organic solvent in the presence of sodium bicarbonate and potassium/sodium bromide under the catalysis of a 2,2,6,6-tetramethylpiperidine oxynitride to prepare a compound of 2-((4R,6S)-2-(furan-2-yl)-6-formacyl-1,3-dioxane-4-yl)acetate (V);
    (5) performing an olefination reaction of the compound V with a (4-p-fluorophenyl-6-isopropyl-2-(N-methyl-methylsulfonylamino)pyrimid-5-yl)-methyl substituted phosphonium salt (IX) or phosphate in the presence of a base to prepare 2-((4R,6S)-6-(trans-2-(4-p-fluorophenyl-6-isopropyl-2-(N-methyl-methylsulfonylamino)pyrimid-5-yl)vinyl)-2-(furan-2-yl)-1,3-dioxane-4-yl)acetate (VI);
    (6) performing acid hydrolysis deprotection of the compound (VI) and then sodium salt formation with a base to prepare rosuvastatin sodium (I);

the synthetic route of the rosuvastatin sodium being:

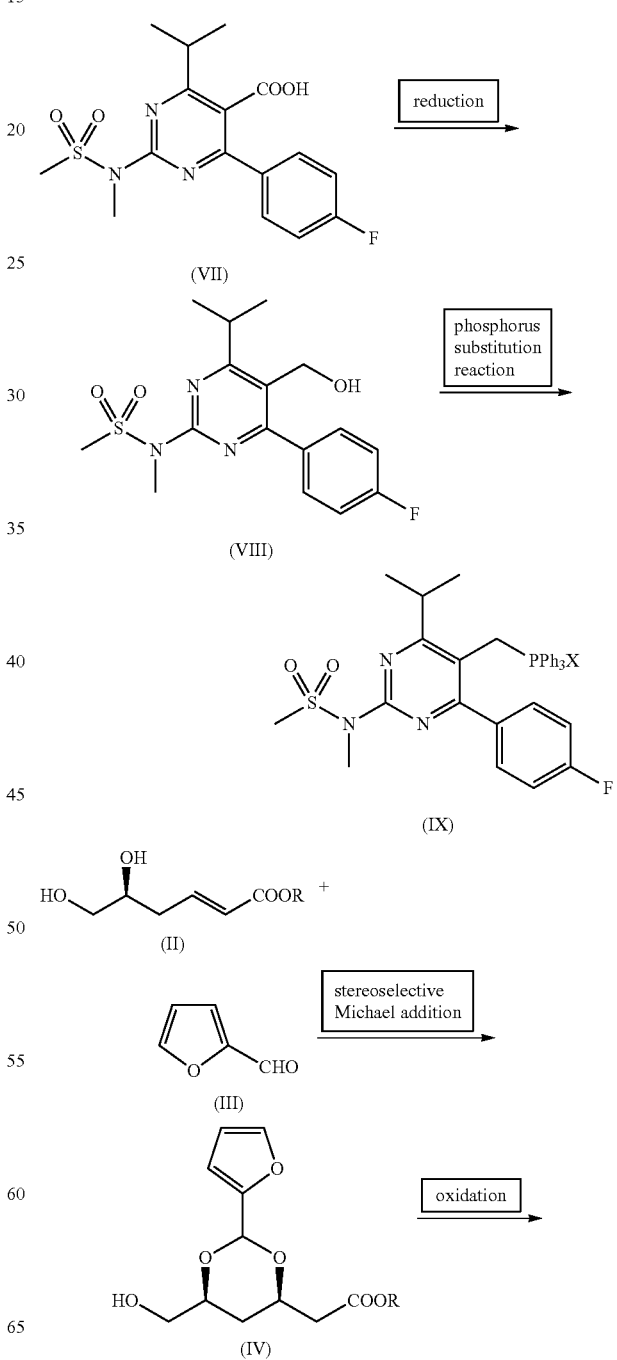

-continued

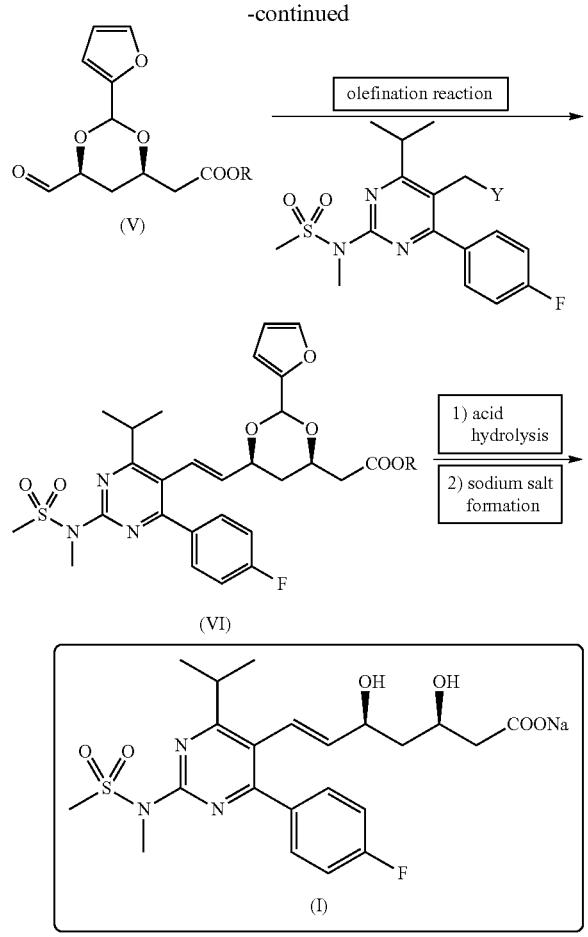

wherein Y is PPh₃X or —PO(OR')₂; X is bromine or boron tetrafluoride; R' is ethyl or isopropyl; and R is a $C_1$-$C_4$ linear or branched alkyl group.

2. The method of claim 1, characterized in that in step (1), the borohydride reducing agent used is sodium borohydride, potassium borohydride, lithium borohydride, zinc borohydride or calcium borohydride, or aluminium borohydride, lithium borohydride, zinc borohydride or calcium borohydride formed in situ in the reaction system of sodium borohydride or potassium borohydride with aluminium chloride, lithium chloride, lithium bromide, zinc chloride or calcium chloride.

3. The method of claim 1, characterized in that in step (1), the alkylchlorosilane used has a structural formula of:

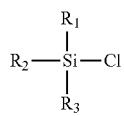

wherein $R_1$, $R_2$ and $R_3$, which is respectively a same or different $C_1$-$C_4$ alkyl group.

4. The method of claim 1, characterized in that in step (1), the assistant used is ceramic debris, glass cullet, gravel or water-washed stone, or processed ceramic beads, glass beads or steel beads.

5. The method of claim 1, characterized in that in step (1), the solvent used is diethyl ether, methyl tert-butyl ether or isopropyl ether, or tetrahydrofuran, 1,4-dioxane, ethylene glycol methyl ether, ethylene glycol dimethyl ether or glycol dimethyl ether.

6. The method of claim 1, characterized in that in step (2), the triphenyl phosphonium salt used is triphenyl phosphonium hydrobromide or triphenyl phosphonium fluoroborate.

7. The method of claim 1, characterized in that in step (2), the solvent used is a $C_1$-$C_4$ polyhalogenated alkane, acetonitrile, benzene, or a $C_1$-$C_3$ alkyl monosubstituted or polysubstituted benzene.

8. The method of claim 1, characterized in that in step (3), the base used is a $C_1$-$C_4$ alkoxide of an alkali metal, or a hexamethyl disilylamide of an alkali metal, the molar ratio of the compound II to the compound III to the base being 1:1-3:0.1-1.2; the organic solvent used is a single solvent of or a mixed solvent of several of a $C_1$-$C_4$ alkane symmetric or asymmetric ether, tetrahydrofuran or dioxane; and the reaction temperature is −40-20° C.

9. The method of claim 8, characterized in that in step (3), the base used is potassium tert-butoxide or sodium hexamethyl disilylamide; the molar ratio of the compound II to the compound III to the base is 1:1-2:0.3-1.2; the organic solvent is tetrahydrofuran or diethyl ether; and the reaction temperature is −40-0° C.

10. The method of claim 1, characterized in that in step (4), the molar ratio of the compound IV to the 2,2,6,6-tetramethylpiperidine oxynitride is 1:0.001-0.05; the organic solvent used is a single solvent of or a mixed solvent of several of a $C_5$-$C_{10}$ alkane or cycloalkane, or a polyhalogenated alkane or arene; and the reaction temperature is −15-10° C.

11. The method of claim 10, characterized in that in step (4), the molar ratio of the compound IV to the 2,2,6,6-tetramethylpiperidine oxynitride is 1:0.001-0.01; the organic solvent used is dichloromethane; and the reaction temperature is −10-5° C.

12. The method of claim 1, characterized in that in step (5), the base used is an alkali metal hydroxide, an alkali metal carbonate, a $C_1$-$C_4$ alkoxide of an alkali metal, or an alkali metal hydride; the molar ratio of the compound V to the (4-p-fluorophenyl-6-isopropyl-2-(N-methyl-methylsulfonylamino)pyrimid-5-yl)-methyl substituted phosphonium salt (IX) or phosphate to the base is 1:0.8-1.2:1-3; the organic solvent used is a single solvent of or a mixed solvent of several of tetrahydrofuran, dioxane, halogenated alkane, an arene, acetonitrile, dimethylsulfoxide, N,N-dimethylformamide or N-methylpyrrolidone; and the reaction temperature is 0-100° C.

13. The method of claim 12, characterized in that in step (5), the base used is potassium carbonate, potassium tert-butoxide or sodium hydride; the molar ratio of the compound V to the (4-p-fluorophenyl-6-isopropyl-2-(N-methyl-methylsulfonylamino)pyrimid-5-yl)-methyl substituted phosphonium salt (IX) or phosphate to the base is 1:0.9-1.1:1-2; the organic solvent used is tetrahydrofuran, acetonitrile, toluene or dimethylsulfoxide; and the reaction temperature is 50-80° C.

14. The method of claim 1, characterized in that in step (6), the acid used is sulphuric acid, hydrochloric acid, trifluoroacetic acid, methylsulphonic acid or p-toluenesulphonic acid; the base used is sodium hydroxide, sodium carbonate, sodium methoxide or sodium ethoxide; the solvent used is a single solvent of or a mixed solvent of several of methanol, ethanol, acetonitrile, acetone, tetrahydrofuran, and water; and the reaction temperature is 0-50° C.

15. The method of claim 14, characterized in that in step (6), the acid used is hydrochloric acid, the base used is sodium hydroxide, and the solvent used is methanol, ethanol or water; and the reaction temperature is 20-40° C.

* * * * *